United States Patent
Takami et al.

(10) Patent No.: US 6,402,688 B1
(45) Date of Patent: Jun. 11, 2002

(54) AIR DELIVERY UNIT FOR ENDOSCOPE

(75) Inventors: Satoshi Takami, Saitama; Junji Usami; Hidehito Kurosawa, both of Tokyo, all of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/428,463

(22) Filed: Oct. 28, 1999

(30) Foreign Application Priority Data

Oct. 29, 1998 (JP) .......................................... 10-308122

(51) Int. Cl.⁷ .............................................. A61B 1/015
(52) U.S. Cl. ................... 600/158; 600/560; 137/565.18
(58) Field of Search ............................ 137/552, 565.18; 600/118, 126, 158, 159, 560

(56) References Cited

U.S. PATENT DOCUMENTS

| | | | | |
|---|---|---|---|---|
| 3,834,392 A | * | 9/1974 | Lampman et al. ...... | 600/126 X |
| 4,865,018 A | * | 9/1989 | Kanno et al. ........... | 600/118 X |
| 4,971,034 A | * | 11/1990 | Doi et al. ............... | 600/158 X |
| 5,249,579 A | * | 10/1993 | Hobbs et al. .......... | 128/662.02 |
| 5,377,688 A | | 1/1995 | Aviv et al. | |
| 5,515,860 A | | 5/1996 | Aviv et al. | |
| 6,095,971 A | * | 8/2000 | Takahashi .................... | 600/159 |
| 6,193,649 B1 | * | 2/2001 | Takami et al. .............. | 600/158 |
| 6,261,227 B1 | * | 7/2001 | Takahashi et al. .......... | 600/158 |
| 6,315,716 B1 | * | 11/2001 | Takami ........................ | 600/158 |
| 6,328,690 B1 | * | 12/2001 | Takami et al. .............. | 600/159 |

* cited by examiner

*Primary Examiner*—John Rivell
(74) *Attorney, Agent, or Firm*—Greenblum & Bernstein, P.L.C.

(57) ABSTRACT

An air delivery unit, in which a closed-space is formed, comprises a discharge-mode switch, a pressure switch and a discharge switch. The discharge-mode switch, the pressure switch, and the discharge switch are arranged on an operation panel. The discharge-mode switch is provided for setting a discharge-mode. The pressure switch is provided for setting the pressure in the closed space. The discharge switch is provided for carrying out a discharge of the air in the closed-space. Accordingly, the discharge-mode switch, the pressure switch and the discharge switch are aligned in operation order.

9 Claims, 7 Drawing Sheets

F I G. 1
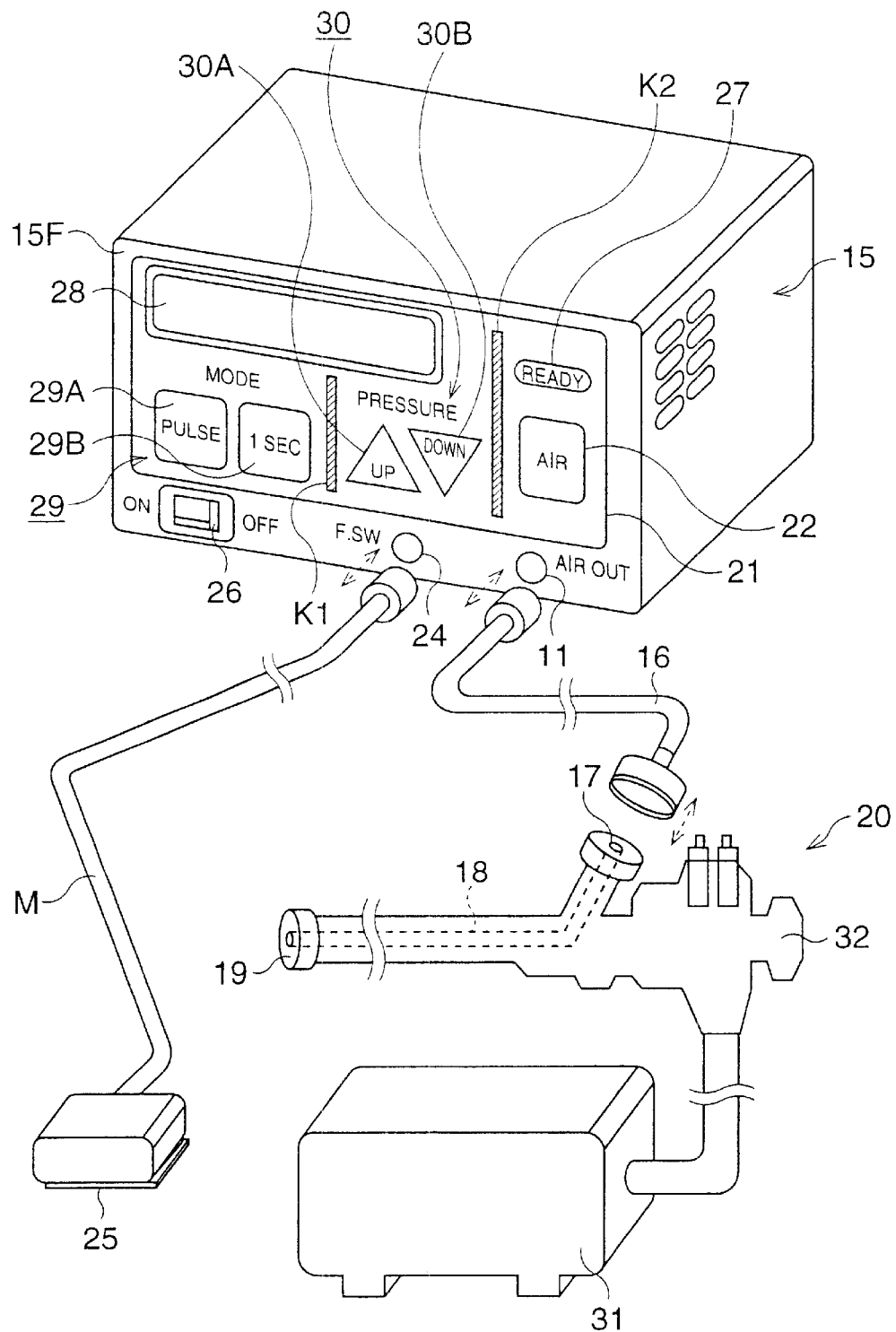

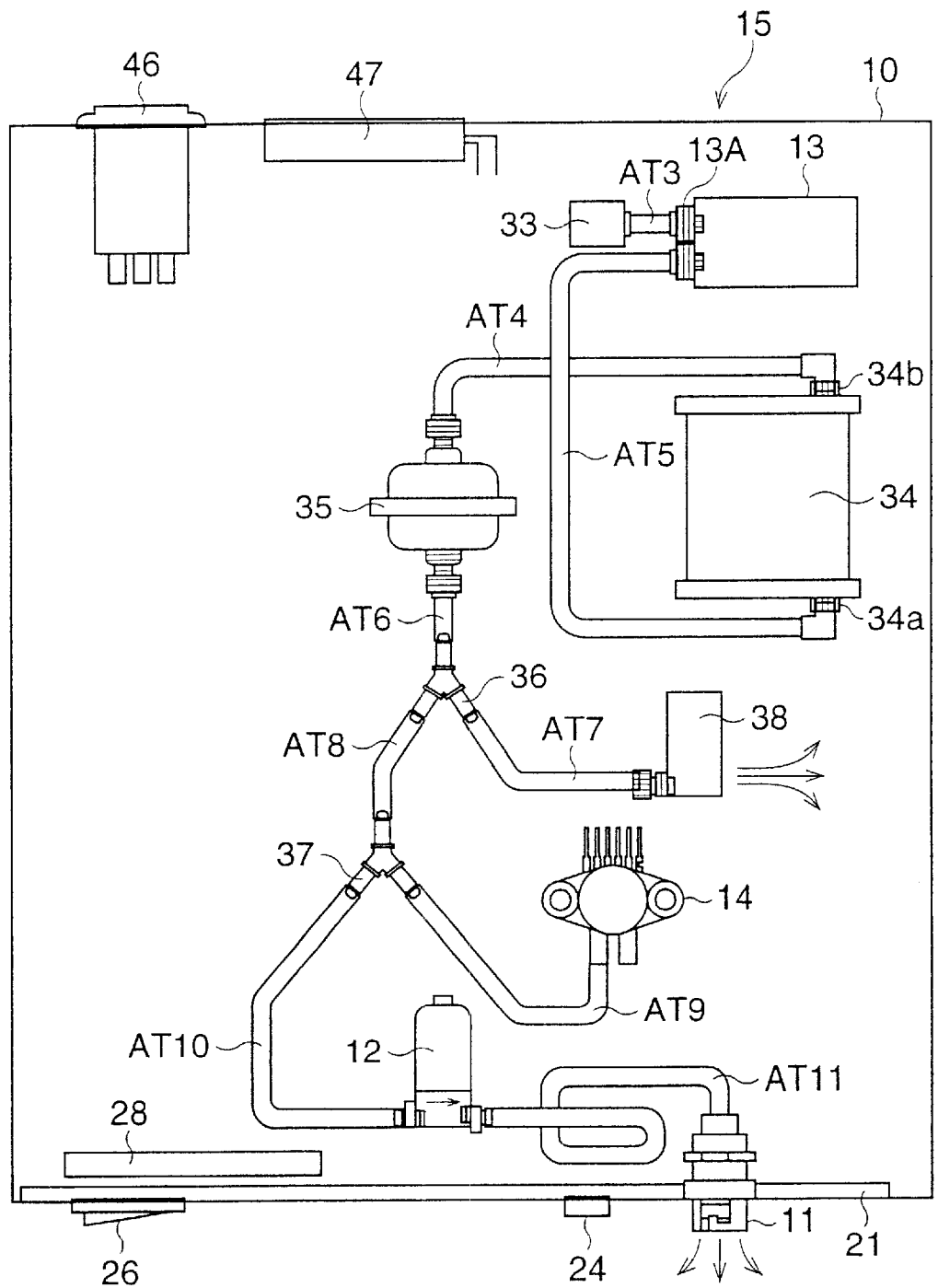
F I G. 3

F I G. 4
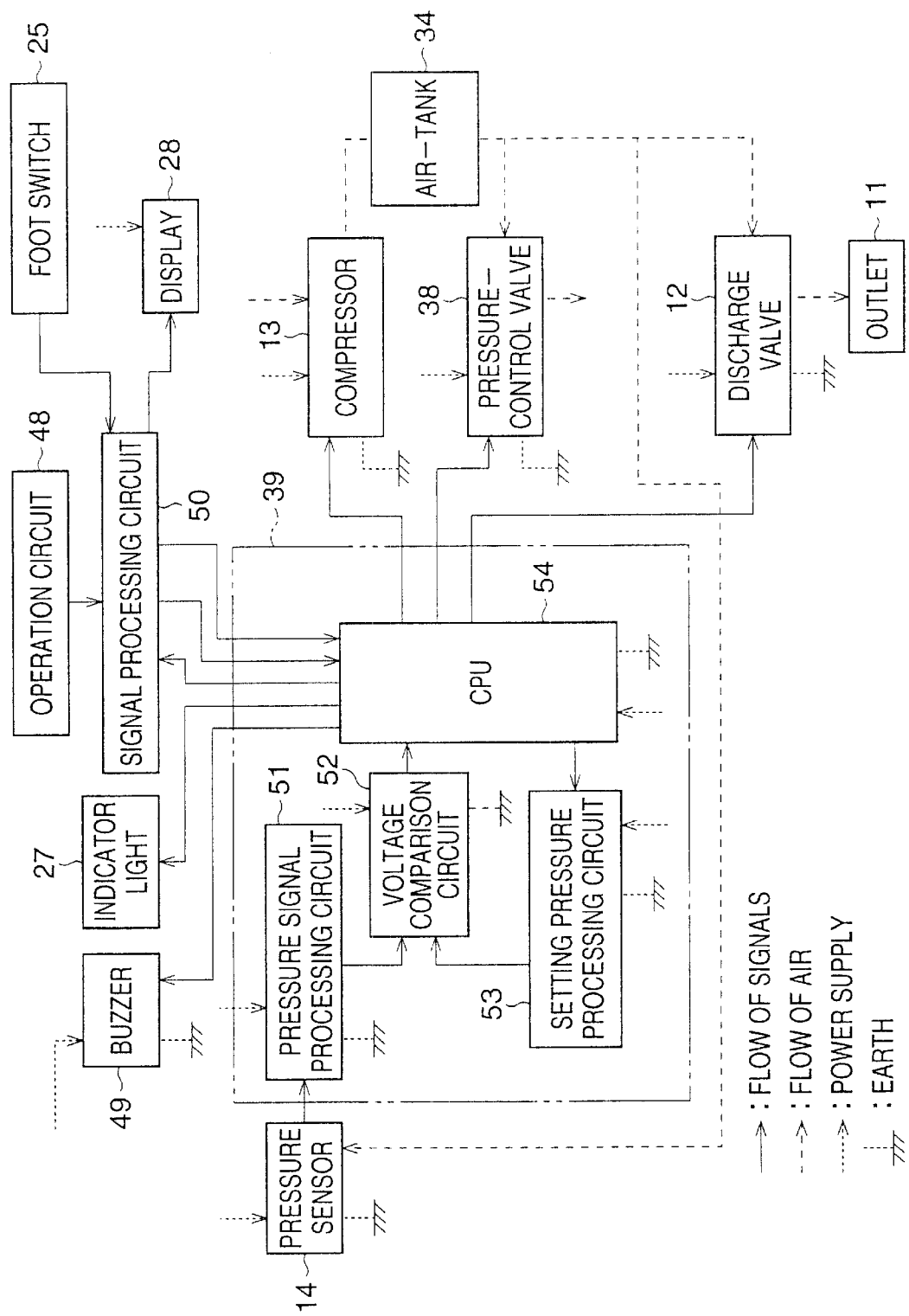

AIR DELIVERY UNIT FOR ENDOSCOPE

BACKGROUND OF THE INVENTION

1. Field of the Invention

This invention relates to an air delivery unit for an endoscope, which delivers air into an organ, such as a stomach. In particular, the present invention relates to an arrangement of switches associated with a discharge of the air.

2. Description of the Related Art

Conventionally, an air delivery unit for an endoscope, which delivers air into a body-cavity of a patient, is known. The air delivery unit comprises a compressor for compressing the air and a valve for regulating an amount of the discharge of the air, whereby the air in the unit is compressed by the compressor, and a puff of air is discharged by opening and shutting the valve. Discharged air is delivered into the organ via a video-scope or an optical fiber-scope, thus a condition of a diseased portion is confirmed.

In general, some switches, including a discharge switch for discharging the air and a compressing switch for compressing the air, are provided on a front surface of the air delivery unit. However, the arrangement of the switches is determined in accordance with the arrangement of the other structural elements provided on the front surface. Namely, the switches are not arranged for ease of operation by an operator. Therefore, the operator occasionally makes errors in operating the switches.

SUMMARY OF THE INVENTION

Therefore, an object of the present invention is to provide an air delivery unit for an endoscope, in which the switches are arranged for ease of operation by the operator. The air delivery unit for an endoscope comprises a discharge-mode switch, a pressure switch, a discharge switch, and an operation panel. In the air delivery unit, a closed-space is formed.

The discharge-mode switch sets a discharge-mode. The pressure switch sets a pressure in the closed-space. The discharge switch carries out a discharge of the air in the closed-space. Accordingly, the discharge-mode switch, the pressure switch and the discharge switch are aligned in operation order, on the operation panel.

BRIEF DESCRIPTION OF THE DRAWINGS

The present invention will be better understood from the description of the preferred embodiments of the invention set forth below together with the accompanying drawings, in which:

FIG. 1 is a perspective view showing an air delivery unit for an endoscope of the first embodiment of the present invention.

FIG. 3 is a view showing structural elements in the air delivery unit.

FIG. 4 is a block diagram of the air delivery unit.

DESCRIPTION OF THE PREFERRED EMBODIMENTS

Figure 2:
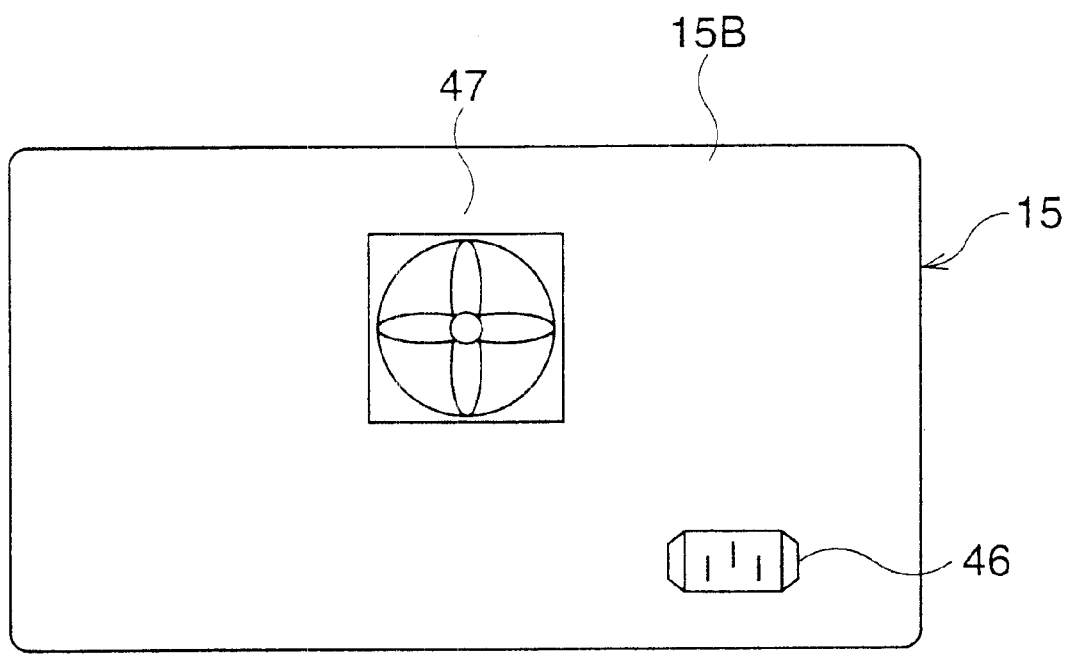
FIG. 2 is a view showing a back surface of the air delivery unit.

Hereinafter, the preferred embodiments of the present invention are described with reference to the attached drawings.

FIG. 1 is a perspective view showing an air delivery unit for an endoscope of a first embodiment of the present invention. This unit is used when an inspection of a diseased portion in an organ, such as a stomach, is performed. Note that, in the air delivery unit, as described later, a closed-space is formed.

In the air delivery unit 15, an operation panel 21, a power switch 26, outlet 11, and a jack 24 are disposed on a front surface 15F. On the operation panel 21, a discharge-mode switch 29 for setting a discharge-mode, a pressure switch 30 for setting a pressure in the closed-space and a discharge switch 22 for carrying out a discharge of air in the closed-space are arranged.

The discharge-mode switch 29 is composed of a pulse switch 29A and a continuity switch 29B. The pulse switch 29A is a switch for discharging one pulse worth of air in the closed-space, in short, a puff of air. The continuity switch 29B is a switch for continuously discharging the air in the closed-space for a predetermined period. In this embodiment, the predetermined period is 1 sec. A mode of a discharge of the air, discharged from the outlet 11, depends on the discharge-mode. In this embodiment, a mode of discharging the puff of the air and a mode of continuously discharging of the air, are applied. When either the pulse switch 29A or the continuity switch 29B is selected by an operator, the discharge-mode is set.

The pressure switch 30 is composed of an up-switch 30A and down-switch 30B. When the up-switch 30A is operated, the pressure in the closed-space is increased. Inversely, when the down-switch 30B is operated, the pressure in the closed-space is decreased. A division marker K1 marks a division between the discharge-mode switch 29 and the pressure switch 30.

An indicator light 27, disposed above the discharge switch 22, indicates a completion of preparation for a discharge of the air. The discharge switch 22 is provided for carrying out a discharge of the air in the closed-space. When the discharge switch 22 is operated, the air in the closed-space is discharged from the outlet 11.

A division marker K2 marks a division between the discharge switch 22 and the pressure switch 30. A display 28 is disposed above the discharge-mode switch 29 and the pressure switch 30, on the operation panel 21. When the pressure switch 30 is operated, a pressure value of the closed-space is displayed on the display 28. A foot switch 25 is connected to the jack 24 via a cord M, whereby a remote control of the discharge of the air can be performed.

A tube 16 is connected to the outlet 11 such that the air in the closed-space is delivered to an electronic endoscope 20. The electronic endoscope 20 comprises the flexible video-scope 32 having an image sensor and the video-processor 31. In the video-scope 32, a forceps tube 18 is provided therethrough, and an end of the tube 16 is detachably connected to a forceps-inlet 17 provided at a proximal end of the video-scope 32. When a medical inspection is performed, the video-scope 32 is inserted into the organ. Then, the air discharged from the outlet 11 is delivered into the video-scope 32 via the tube 16, and the air is discharged from a forceps-outlet 19 provided at a distal end of the video-scope 32.

The video-scope 32 is connected to the video-processor 31, and a monitor (not shown) is also connected to the video-processor 31. The object image is formed on the image sensor provided at the distal end of the video-scope 32, and is converted into image signals by photoelectric conversion. The image signals are fed to the video-processor 31, thus, the object image is displayed on the monitor.

FIG. 2 is a view showing a back surface of the air delivery unit 15. On the back surface 15B, a fan 47 and an AC inlet 46 are provided. The fan 47 sends outer air into the air delivery unit 15 to cool the air in the closed-space. Electric power is supplied to the air delivery unit 15 through the inlet 46.

FIG. 3 is a view showing an arrangement of main structural elements provided in the air delivery unit 15. The AC inlet 46, the power switch 26, and the operation panel 21 including the display 28 are respectively disposed on housing 10 of the air delivery unit 15.

In the housing 10, the closed-space is formed by linking a compressor 13, an air-tube AT5, an air-tank 34, an air-tube AT4, an air-filter 35, an air-tube AT6, a connector 36, an air-tube AT7, a pressure-control valve 38, an air-tube AT8, a connector 37, an air-tube AT9, a pressure-sensor 14, an air-tube AT10, and a discharge valve 12 together. The air in the closed-space is not discharged except when the pressure-control valve 38 or the discharge valve 12 opens. The pressure-control valve 38 is closed except when an adjustment of the pressure in the closed-space is performed. Similarly, the discharge valve 12 is closed except when the air in the closed-space is discharged.

A silencer 33, which is provided for suppressing noise generated from the compressor 13, is connected to the compressor 13 via an inlet 13A. When the compressor 13 operates, outside air is inhaled into the compressor 13, that is, the closed-space, via the silencer 33 and the air-tube AT3. At this time, the inhaled air is compressed. Thus, the pressure in the closed-space is enhanced. The compressor 13 is connected to the air-tank 34 through the air-tube AT5.

The air-tank 34 is provided to enlarge the volume of the closed-space. The volume of the air-tank 34 is larger than the total volume of the air-tubes AT4 to AT10. The air-tank 34 has an inlet 34a, to which the air-tube AT5 is connected, and an outlet 34b, to which the air-tube AT4 is connected. The air filter 35, to which the air-tank 34 is connected through the air-tube AT4, is provided for removing dust from the closed-space.

The closed-space forks at the connector 36, and the air-tube AT7 is extended toward the pressure-control valve 38. The pressure-control valve 38 is provided for adjusting the pressure in the closed-space. Further, the closed-space forks at the connector 37 and the air-tube AT9 is extended toward the pressure-sensor 14. The pressure-sensor 14 is provided for measuring the pressure in the closed-space.

When the pressure switch 30 (shown in FIG. 1) is operated, the pressure-control valve 38 opens and the compressor 13 are driven, on the basis of the pressure measured by the pressure-sensor 14. Namely, the pressure in the closed-space is adjusted so as to equal a setting pressure, set by the operation of the pressure switch 30. For example, when the pressure in the closed-space is low compared with the setting pressure, the compressor 13 is driven to enhance the pressure, while the pressure-control valve 38 remains closed. On the other hand, when the pressure in the closed-space is high compared with the setting pressure, the pressure-control valve 38 opens and shuts to emit the air in the closed-space, while the compressor does not act. When the pressure in the closed-space equals the setting pressure, the pressure-control valve 38 shuts and the compressor 13 stops.

When the discharge switch 22 or the foot switch 25 is operated after the pressure in the closed-space is adjusted, the discharge valve 12 opens, so that the air in the closed-space is discharged from the outlet 11 via the air-tube AT11.

Note that, a timing of an open-close of the discharge valve 12 depends on the discharge-mode. Namely, when the pulse switch 29A is selected, the discharge valve 12 opens and closes such that a puff of air is discharged. On the other hand, when the continuity switch 29B is selected, the discharge valve opens for 1 sec.

FIG. 4 is a block diagram of the air delivery unit 15. A control system circuit 39 comprises a pressure signal processing circuit 51, a voltage-comparison circuit 52, a setting pressure signal processing circuit 53, and a CPU 54. The control system circuit 39 controls the air delivery unit 15 as a whole. In the CPU 54, control-signals are output to the compressor 13, the discharge valve 12, the pressure-control valve 38, and a buzzer 49.

In an operation circuit 48, operation-signals are generated when one of the discharge switch 22, the pressure switch 30, and the discharge-mode switch 29 is operated. The operation-signals, output from the operation circuit 48 or the foot switch 25, are subjected to various processes in a signal processing circuit 50, and then fed to the CPU 54. A setting pressure signal, corresponding to the setting pressure, is fed from the CPU 54 to the display 28 via the signal processing circuit 50. Thus, the value of the setting pressure is displayed on the display 28.

A pressure signal, corresponding to the pressure in the closed-space, is fed from the pressure-sensor 14 to the pressure signal processing circuit 51. In the pressure signal processing circuit 51, the pressure signal is subject to various signal processes, such as a reduction of a reset noise, and then is fed to the voltage-comparison circuit 52. On the other hand, the setting pressure signal is input to the setting pressure signal processing circuit 53 via the CPU 54.

In the voltage comparison circuit 52, the pressure signal output from the signal processing circuit 51 is compared with the setting pressure signal output from the setting pressure signal processing circuit 53. Namely, the pressure in the closed-space at the present is compared with the setting pressure. Then, a difference signal, corresponding to the difference between the pressure and the setting pressure, is generated and then is fed to the CPU 54. In the CPU 54, the control-signal is fed to the pressure-control valve 38 or the compressor 13 on the basis of the difference signal, thus the compressor 13 or the pressure-control valve 38 is driven.

Note that, to prevent a hunting-situation, in which the compressor 13 and the pressure-control valve 38 acts for a long time, from occurring, the pressure-control valve 38 and the compressor 13 is not driven when the difference signal is under a predetermined range of the voltage.

In the buzzer 49, a buzzer, associated with the operation of the switches, sounds. The indicator light 27 radiates when the preparation for the discharge of the air is finished.

Note that the electric power is supplied to the display 28, the pressure-sensor 14, the CPU 54, the compressor 13, and the discharge valve 12 through a power supply circuit (not shown), respectively.

Figure 5:
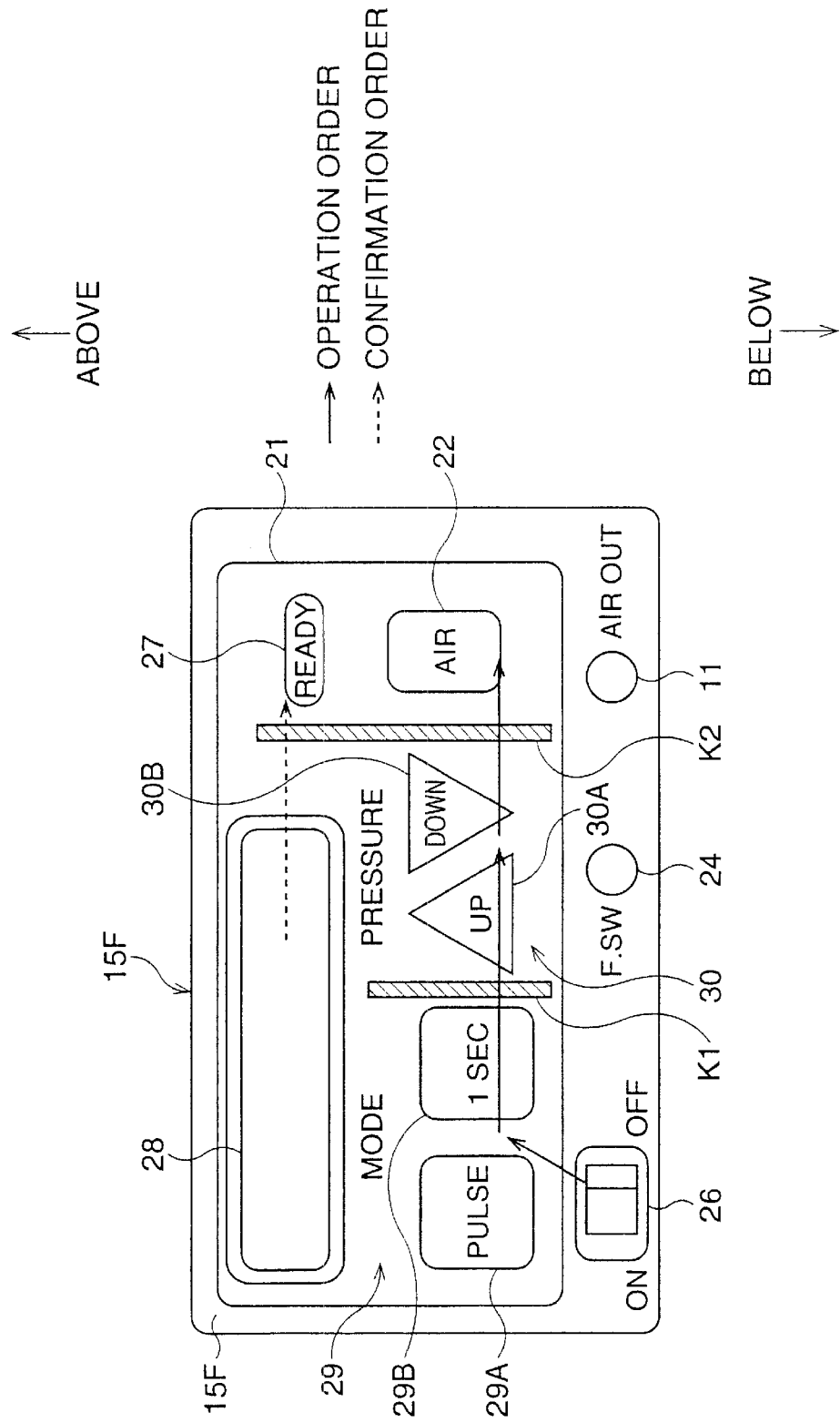
FIG. 5 is an elevation view showing a front surface of the air delivery unit.

FIG. 5 is a elevation view showing the front surface 15F of the air delivery unit 15. Note that a solid arrow indicates an operation order of the switches, and a broken arrow indicates a confirmation order by the operator.

After the power switch 26 is turned ON, firstly, the discharge-mode is set. Namely, either the pulse switch 29A or the continuity switch 29B is selected by the operator. Next, the pressure in the closed-space is adjusted to equal the setting pressure, which is set by operating the up-switch 30A and/or down-switch 30B. Then, when the indicator light 27 is turned on in order to indicate that the preparation for the discharging of the air is finished, the discharge switch 22 is finally operated, thus the air in the closed-space is discharged from the outlet 11. In this embodiment, the discharge-mode switch 29, the pressure switch 30, and the discharge switch 22 are aligned in operation order. Therefore, by operating these switches on the operation panel 21 along one direction, i.e., the solid arrow direction, the air is discharged from the outlet 11. The operator had no difficulty confirming the position of each switch on the operation panel 21.

The discharge-mode switch 29 and the pressure switch 30 are discriminated by the division marker K1. Similarly, the pressure switch 30 and the discharge switch 22 are discriminated by the division marker K2. Therefore, the operator can easily discriminate between each switch on the operation panel 21.

The display 28 is arranged above the pressure switch 30 and the discharge switch 22, further the indicator light 27 is disposed near the display 28. Thus, during operation of the pressure switch 30 and the discharge switch 22, the pressure value and the indicator light 27 can be easily confirmed by the operator, as the direction of the operation order corresponds to the direction of the confirmation order.

As described above, the pressure-mode switch 29, the pressure switch 30, and the discharge switch 22 are aligned in operation order. Thus, when the discharge of the air is performed, the operator can securely operate these switches, without error.

Figure 6:
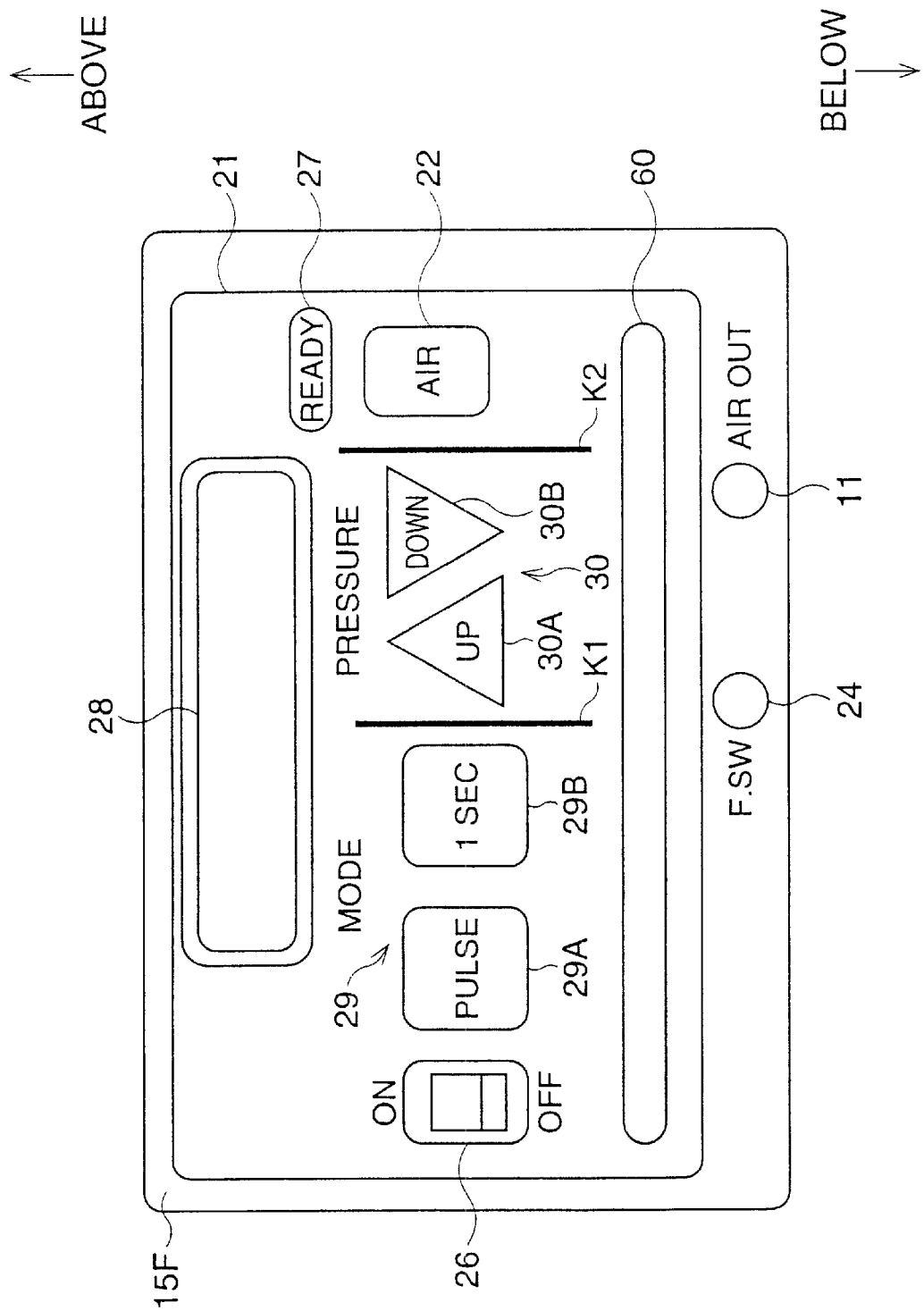
FIG. 6 is an elevation view showing an air delivery unit for an endoscope of the second embodiment of the present invention.
Figure 7:
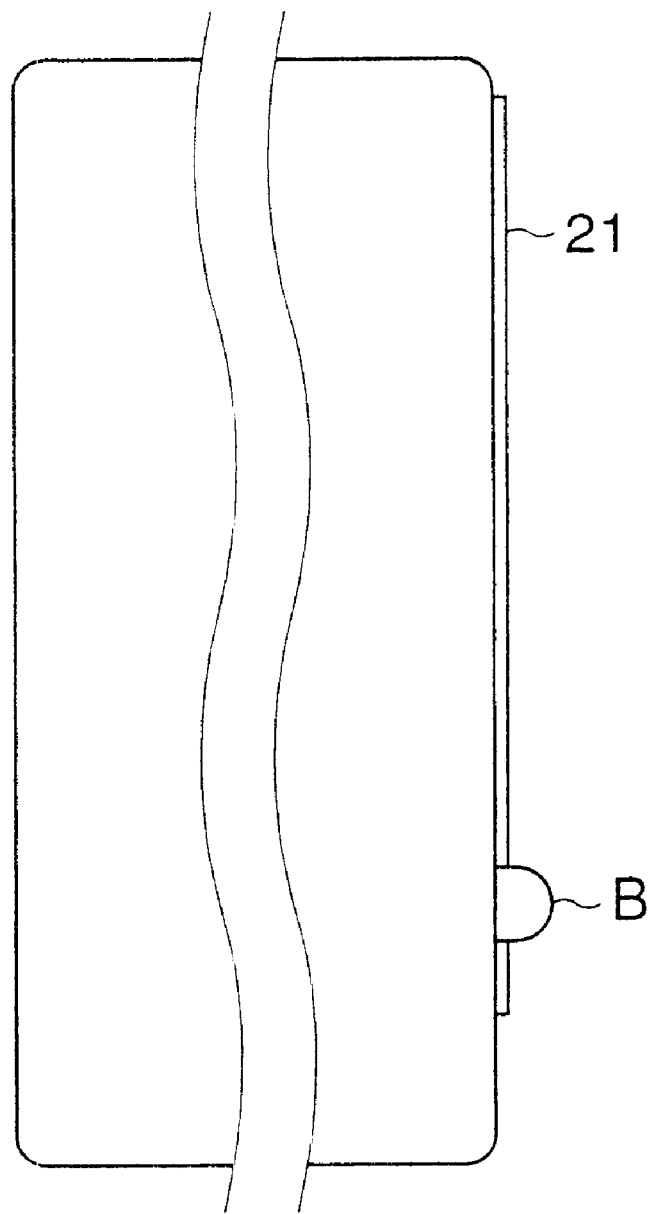
FIG. 7 is a side view of the air delivery unit.

FIGS. 6 and 7 show a second embodiment. The second embodiment is different from the first embodiment in case of the arrangement of switches. Since other portions are similar to those of the first embodiment, designations remain the same and descriptions are omitted.

FIG. 6 is a elevation view of the air delivery unit 15. FIG. 7 is a side view of the air delivery unit 15.

As shown in FIG. 6, the power switch 26 is disposed on the operation panel 21. Further, a protrusion member 60 is aligned along the arrangement of switches.

The protrusion member 60 projects from the operation panel 21 (shown in FIG. 7), thus the operator can recognize the protrusion member 60 when the operator touches the protrusion member 60 by hand. Further, the protrusion member 60 extends along an alignment of the switches on the operation panel 21, such that all of the switches on the operation panel 21 are on one side of the protrusion member 60. Note that, the gap between the protrusion member 60 and each switch on the operation panel 21 is approximately equal to the gap between the tip of the thumb and the tip of the index finger of the operator. Preferably, the gap between the protrusion member 60 and each switch is from 8 centimeters to 15 centimeters. Further preferably, the gap between the protrusion member 60 and each switch is about 10 centimeters.

When the switches on the operation panel 21 are operated for discharging the air in the closed-space, the operator operates the switches with the index finger while touching the protrusion member 60 with the thumb. Namely, the protrusion member 60 guides an operation direction of the switches. Therefore, in addition to the effect of the first embodiment, the operator can more easily operate the switches with the aid of the protrusion member 60.

In a modification, a concave or a convex portion may be formed on the protrusion member 60, such that the position of the concave or the convex portion corresponds to the position of the division marker K1 and K2. Thus, the operator can confirm the operation order more easily.

Further, the concave or the convex portion may be formed on the protrusion member 60 such that the position of the concave or the convex portion corresponds to the position of each switch on the operation panel 21.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No. 10-308122 (filed on Oct. 29, 1998) which is expressly incorporated herein, by reference, in its entirety.

What is claimed is:

1. An air delivery unit for an endoscope, in which a closed-space is formed, that discharges air in said closed-space, said air delivery unit comprising:

a discharge-mode switch that sets a discharge-mode of the air discharged from said closed-space;

a pressure switch that sets a pressure in said closed-space;

a discharge switch that carries out the discharge of the air in said closed-space, whereby the air in said closed-space is discharged; and an operation panel, on which said discharge switch, said pressure switch and said discharge-mode switch are arranged, said discharge-mode switch, said pressure switch and said discharge switch being aligned on said operation panel in the order, in which said discharge-mode switch, said pressure switch and said discharge switch are operated.

2. The air delivery unit for an endoscope of claim 1, further comprising an indicator light, arranged above said discharge switch on said operation panel, that radiates to indicate that adjustment of the pressure in said closed-space is completed and said air delivery unit is prepared for discharge of the air.

3. The air delivery unit for the endoscope of claim 1, wherein division markers marks divisions on said operation panel, that discriminate discharge-mode switch, said pressure switch and said discharge switch, respectively.

4. The air delivery unit for the endoscope of claim 1, wherein said discharge-mode switch is composed of a pulse switch that carries out a discharge of a puff of the air in said closed-space and a continuity switch that carries out a continuous discharge of the air in said closed-space for a predetermined period.

5. The air delivery unit for the endoscope of claim 4, wherein said continuity switch carries out the continuous discharge of the air in said closed-space for 1 sec.

6. The air delivery unit for the endoscope of claim 1, wherein said pressure switch is composed of an up-switch that increases the pressure in said closed-space and a down-switch that decreases the pressure in said closed-space.

7. The air delivery unit for the endoscope of claim 1, further comprising a display, arranged above said discharge-mode switch and said pressure switch on said operation panel, that displays a value of a setting pressure in said closed-space, set by an operation of said pressure switch.

8. An air delivery unit for an endoscope, in which a closed-space is formed, that discharges air in said closed-space, said air delivery unit comprising:

a discharge-mode switch that sets a discharge-mode;

a pressure switch that sets pressure in said closedspace;

a discharge switch that carries out a discharge of air in said closed-space;

an operation panel, on which said discharge switch, said pressure switch, said discharge-mode switch and a protrusion member are arranged; and said protrusion member, extending along an alignment direction of said discharge-mode switch, said pressure switch and said discharge switch, and projecting from said operation panel, said discharge-mode switch, said pressure switch and said discharge switch being aligned on said operation panel in the order, in which said discharge-mode switch, said pressure switch and said discharge switch are operated.

9. The air delivery unit for the endoscope of claim 8, wherein said protrusion member is disposed below said discharge-mode switch, said pressure switch and said discharge switch, on said operation panel.

* * * * *